(12) United States Patent
Cumming

(10) Patent No.: US 8,080,056 B2
(45) Date of Patent: *Dec. 20, 2011

(54) LENS ASSEMBLY FOR DEPTH OF FOCUS

(75) Inventor: J. Stuart Cumming, Laguna Beach, CA (US)

(73) Assignee: C & C Vision International, Ltd., Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 12/822,067

(22) Filed: Jun. 23, 2010

(65) Prior Publication Data

US 2010/0262235 A1  Oct. 14, 2010

Related U.S. Application Data

(62) Division of application No. 10/856,313, filed on May 27, 2004, now abandoned, which is a division of application No. 09/574,441, filed on May 19, 2000, now Pat. No. 6,849,091.

(51) Int. Cl.
A61F 2/16 (2006.01)

(52) U.S. Cl. ...... 623/6.21; 623/6.41; 623/6.44

(58) Field of Classification Search ........ 623/6.18–6.21, 623/6.34, 6.37, 6.38, 6.4–6.44, 6.46, 6.47, 623/6.49, 6.51–6.55
See application file for complete search history.

(56) References Cited

U.S. PATENT DOCUMENTS

| | | | |
|---|---|---|---|
| 4,704,123 A | 11/1987 | Smith | |
| 4,892,543 A | 1/1990 | Turley | |
| 4,932,966 A | 6/1990 | Christie et al. | |
| 6,051,024 A | 4/2000 | Cumming | |
| 6,616,692 B1 | 9/2003 | Glick et al. | |

FOREIGN PATENT DOCUMENTS

| | | |
|---|---|---|
| DE | 3626869 A1 | 2/1988 |
| EP | 0194390 A1 | 9/1986 |
| EP | 0336877 A1 | 10/1989 |
| FR | 2728458 A1 | 6/1996 |
| FR | 2728459 A1 | 6/1996 |
| FR | 2734472 A1 | 11/1996 |
| GB | 2226246 A | 6/1990 |
| RU | 2026040 C1 | 1/1995 |
| RU | 2026652 C1 | 1/1995 |
| WO | WO 97/12564 A1 | 4/1997 |

*Primary Examiner* — David H. Willse
(74) *Attorney, Agent, or Firm* — Orrick, Herrington & Sutcliffe LLP

(57) ABSTRACT

An intraocular lens assembly for increased depth of focus has a frame configurated to vault posteriorly in an eye and an optic attached thereto. Pressure from ciliary muscle contraction moves the optic anteriorly to focus the eye for near vision.

2 Claims, 4 Drawing Sheets

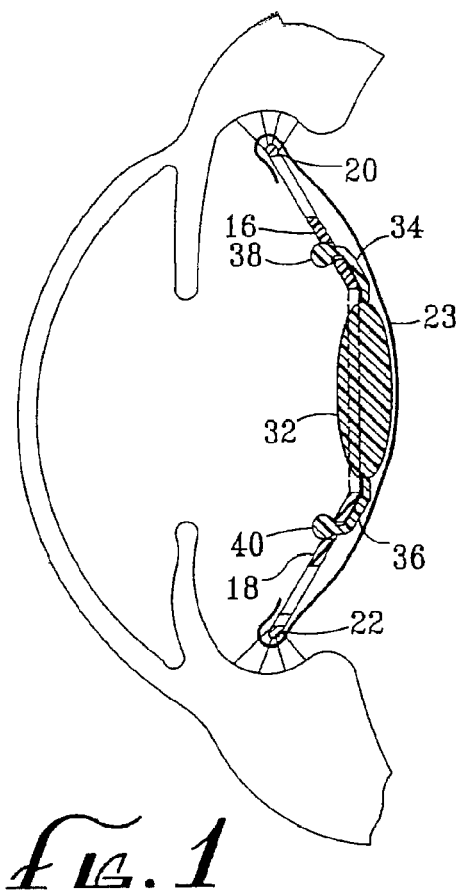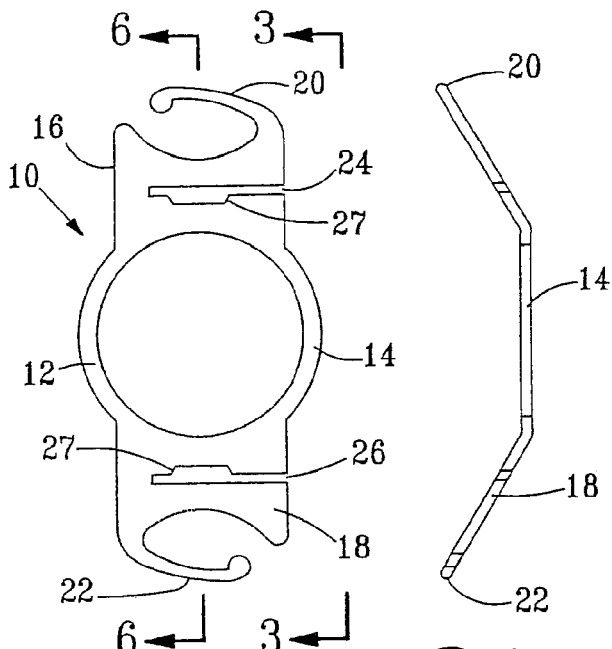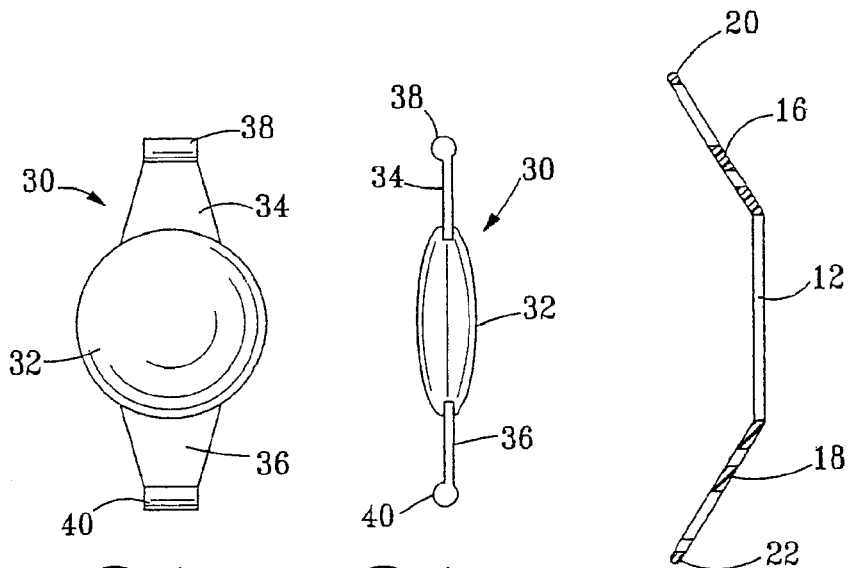

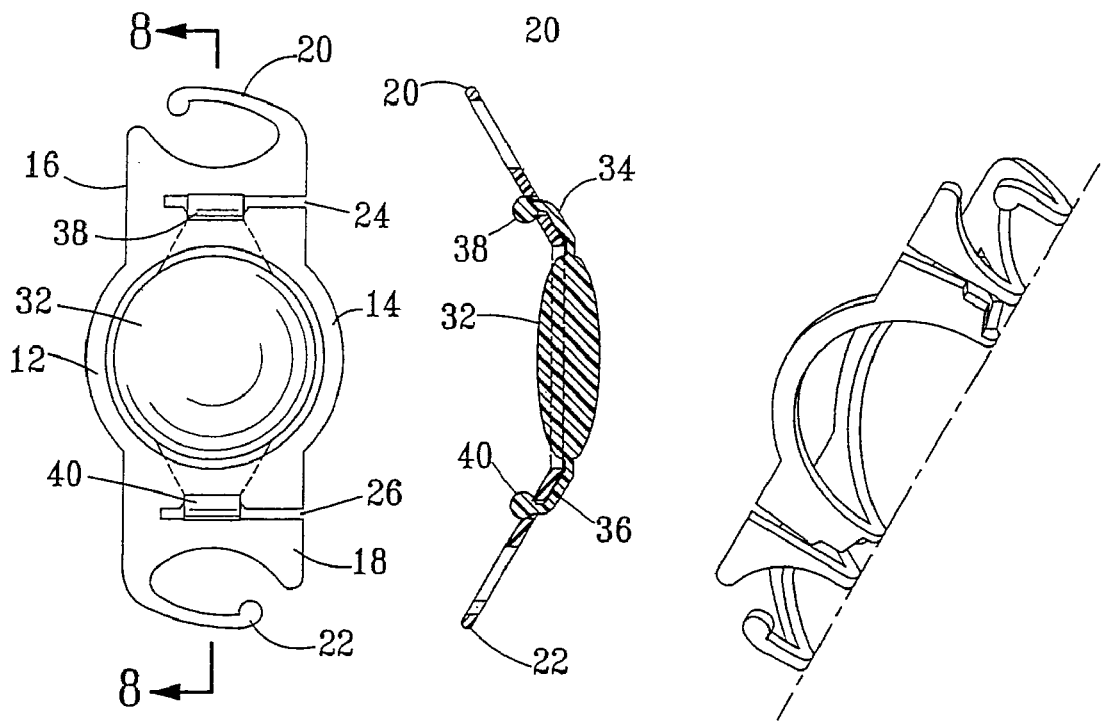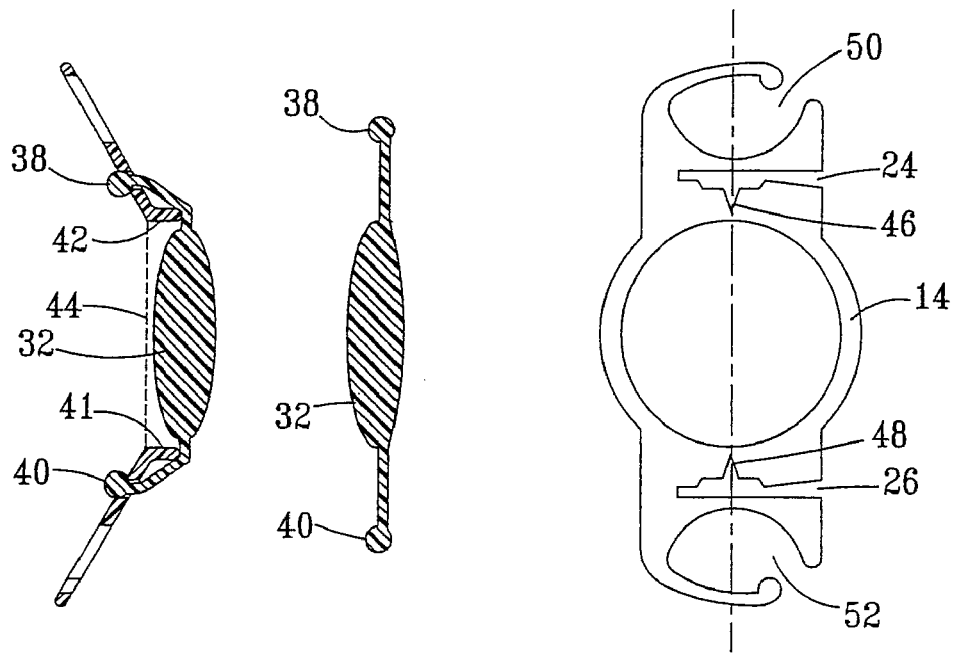

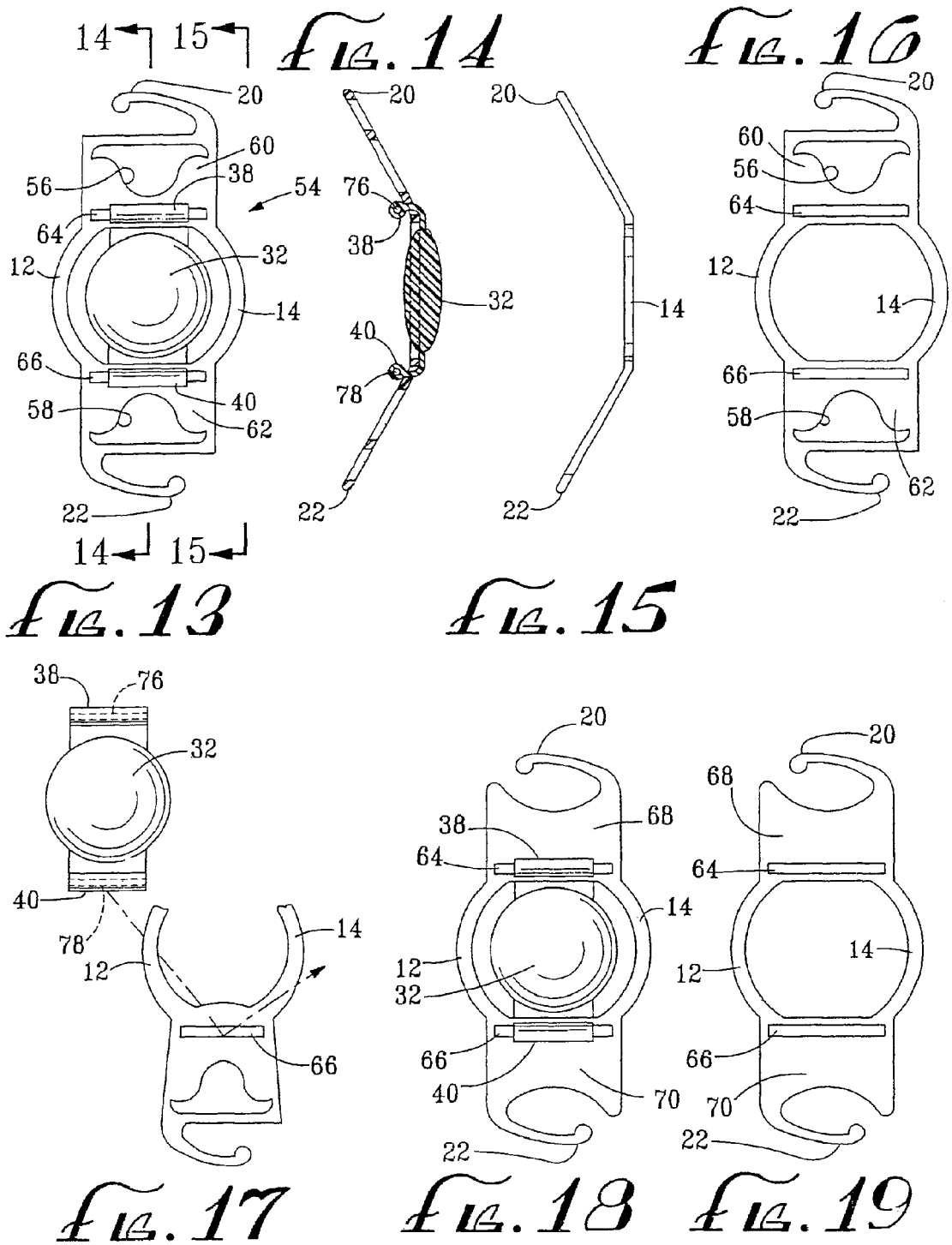

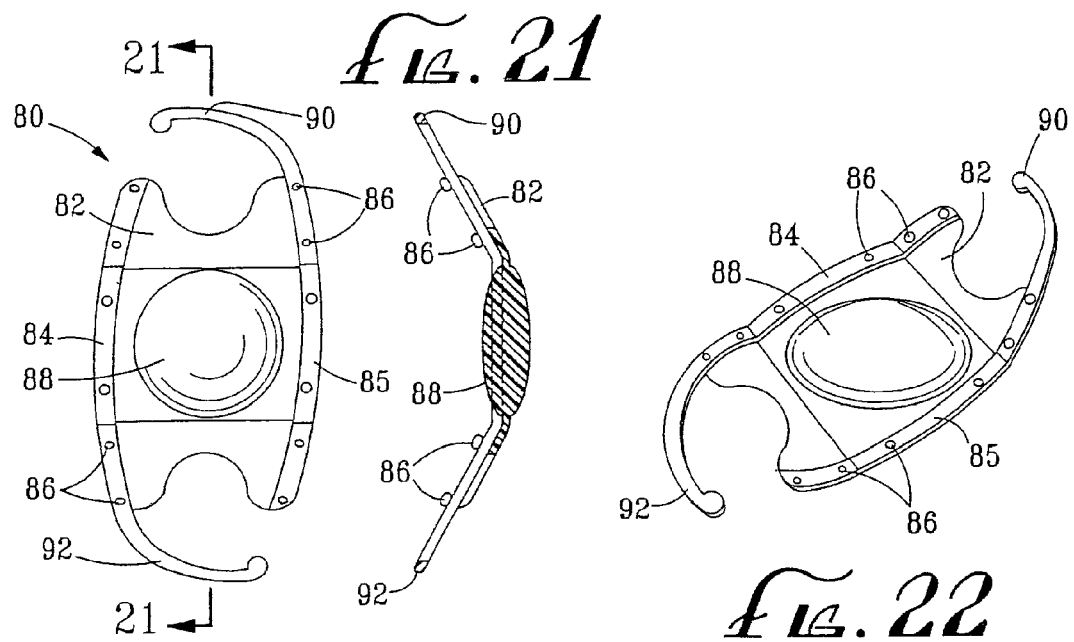
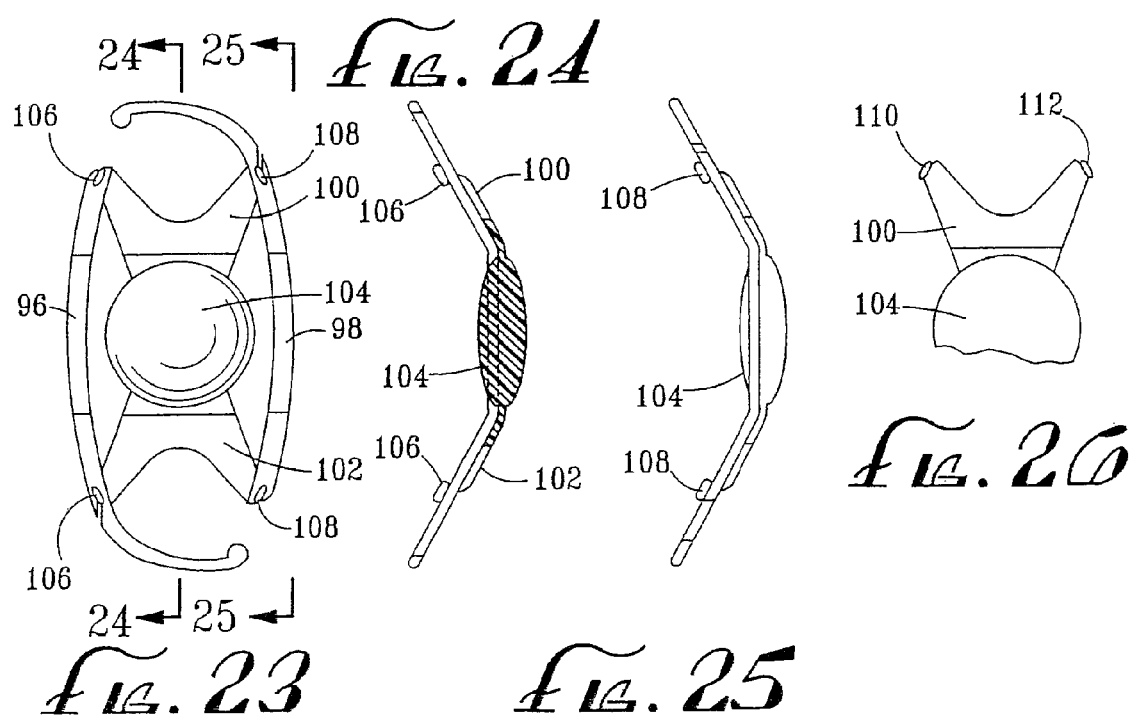

LENS ASSEMBLY FOR DEPTH OF FOCUS

CROSS REFERENCE TO RELATED APPLICATIONS

This application is a divisional of and claims priority to U.S. application Ser. No. 10/856,313 filed May 27, 2004 (now abandoned), which is a divisional of U.S. application Ser. No. 09/574,441 filed May 19, 2000, now U.S. Pat. No. 6,849,091, the disclosure of which is fully incorporated herein by reference.

BACKGROUND OF THE INVENTION

The present invention provides increased depth of focus by positioning an optic posteriorly in the eye by disposing it on a substantially rigid frame which is configurated to vault posteriorly, thus enabling accurate viewing over a. wider range of distances with greater distance between the cornea and the optic, and the further posteriorly the positioning of the optic, the higher the power of the optic, and the less the lens movement required for a given power change.

The frame may preferably have plate haptics with transversely extending loops at the outer ends of the haptics to engage peripheral portions of the capsular bag of the eye and center the lens. The haptics may preferably be such as that shown and described in Applicant's U.S. Pat. No. 6,051,024, "Intraocular Lenses with Fixated Haptics".

The optic utilized with the invention is substantially smaller than the natural human lens. Whereas the natural human lens is about 5.0 mm in thickness, an optic utilized with the invention may typically be 1.0 mm, and may range between 0.5 mm and 1.5 mm. The optic may preferably be similar to that shown and described in Applicant's application Ser. No. 09/370,235, "Lens For Increased Depth of Focus."

BRIEF DESCRIPTION OF THE DRAWINGS

FIG. 1 is a sectional view of a preferred embodiment of the invention disposed in an eye;

FIG. 2 is an elevational view of a frame utilized with the invention;

FIG. 3 is a sectional view taken at line 3-3 in FIG. 2;

FIG. 4 is an elevational view of an lens utilized with the invention and having extensions with transverse ridges thereon;

FIG. 5 is a side view of the lens of FIG. 4;

FIG. 6 is a sectional view taken at line 6-6 in FIG. 2;

FIG. 7 is an elevational view of the components of FIGS. 2 and 4 in assembled relation;

FIG. 8 is a sectional view taken at line 8-8 in FIG. 7;

FIG. 9 is a sectional view, similar to that of FIG. 8, further showing a modified form with extending edge portions of haptics;

FIG. 10 is a sectional view of the lens in FIG. 5, extended and unassembled;

FIG. 11 is an elevational view of a modified form of the frame of FIG. 2;

FIG. 12 is a perspective view showing the lens assembly of FIG. 7 folded along its longitudinal axis;

FIG. 13 is an elevational view of a modified form of the lens assembly of FIG. 7;

FIG. 14 is a sectional view taken at line 14-14 in FIG. 13;

FIG. 15 is an edge view of the frame of FIGS. 13 and 14;

FIG. 16 is an elevational view of the frame portion of the assembly of FIG. 13;

FIG. 17 is an exploded view of a frame with a modified lens wherein hand ridge portions thereof have passages therethrough for axial compression;

FIG. 18 shows a modified form of the lens assembly of FIG. 13;

FIG. 19 is an elevational view showing the frame component of the lens of FIG. 18;

FIG. 20 is an elevational view of a lens of the invention wherein frame members are joined with a web having an optic thereon;

FIG. 21 is a sectional view taken at line 21-21 in FIG. 20;

FIG. 22 is a perspective view of the lens of FIG. 20;

FIG. 23 is an elevational view of a modified form of the lens of FIG. 20, wherein oppositely extending web portions are bifurcated and engaged with the frame members;

FIG. 24 is a sectional view taken at line 24-24 in FIG. 23;

FIG. 25 is an edge side view of the lens of FIG. 23; and

FIG. 26 is a partial elevational view of a portion of the lens of FIG. 23, showing lug portions at the outer ends of a bifurcated web portion.

DETAILED DESCRIPTION OF THE INVENTION

The present invention provides increased depth of focus by providing a relatively rigid frame with haptics extending oppositely to engage a perimeter or equator of a capsular bag, and having a central opening to accommodate an optic engaged on the frame and movable anteriorly relative to the frame.

Referring to FIGS. 1 to 8, frame 10 comprises a central portion 12 which defines a relatively large opening 14, and haptics 16, 18 extending oppositely from the central portion with fixation loops 20, 22 extending transversely from their outer portions, as shown, to engage peripheral portions of capsular bag 23. Slots 24, 26 extend from outer edges of the respective haptics and across a major width of each haptic.

A lens 30 comprises an optic 32 from which extend relatively short extensions 34, 36 which terminate in generally cylindrical ridges 38, 40. The ridges are adapted to be engaged and retained in the slots 24, 26, as shown in FIGS. 7 and 8, wherein they are retained in position by shoulders 27 which define enlarged portions of the slots 24, 26 (FIG. 2).

In the modified form of FIGS. 9 and 10 posteriorly extending frame portions or bumps 42, position the optic 32 further posteriorly than it would otherwise be, thus to effect additional, enhanced depths of focus, as will be understood from the geometry of the components.

In FIGS. 7, 8 and 9, the frame 10 and lens 30 are shown retained in assembled relation.

The optic 32 is thinner than a natural optic of a human eye and may have a thickness between 0.50 mm and 1.5 mm and may typically be about 1.0 mm thickness. The optic may typically be similar to that shown and described in the above-mentioned application of Applicant.

In operation, the optic 32 is movable anteriorly of the eye under vitreous pressure upon constriction of the ciliary muscle. The contraction of the muscle produces vitreous pressure which tends to urge the optic toward or into the hole 14 of the frame. The optic typically need not extend through the opening 14, but only extend about 1.0 mm into the opening. The optic need only move 1.0 mm to effect a change of 1.5 to 2.0 diopters of power change. The relatively rigid frame and the vitreous pressure thus effect optic movement relative to the frame.

It may be noted that an advantage of the present invention is that utilization of the relatively rigid frame substantially eliminates need for administration to a patient of a substance such as atropine during a period following surgery. This eliminates a problem in practice relative to patients not taking atropine, as instructed, during a period following surgery in order to maintain the ciliary muscle in a relaxed condition during fibrosis relative to end portions of haptics.

The transversely extending loops 20, 22 provide centration and to facilitate fixation of the optic in the general manner described in Applicant's U.S. Pat. No. 6,051,024, entitled "Intraocular Lenses With Fixated Haptics".

The frame 10 may typically be formed of PMMA, polycarbonate, nylon, other relatively rigid material, platinum or gold. The lens 30 may preferably be formed of a flexible optical material, such as silicone, acrylic, HENNA, hydrogel, etc.

To provide for the bending or folding of the frame, as shown in FIG. 12, for insertion through a relatively short slit in the eye of a patient, the frame may be formed of relatively soft material at portions of the frame which are folded to provide a narrower configuration for insertion through the relatively short slit of the eye. These features include notches 46, 48 (FIG. 11) which extend from respective slots 24, 26 toward the opening 14 of the frame, and substantially reduced portions 50, 52 outwardly of the slots 24, 26.

Referring to FIGS. 13-17, a lens 54 has features in common with the embodiment of FIGS. 7-11, and differs in having enlarged openings 56, 58 of the configuration shown, wherein an enlarged rounded portion of the opening extends to define relatively narrow haptic portions 60, 62 wherein slots 64, 66 are defined to receive ridges 38, 40, as with the embodiment of FIGS. 7-11. The defining of the narrow haptics portions facilitates bending of the lens about its longitudinal axis (FIG. 12). FIG. 17 shows a partial, exploded view of this embodiment.

FIGS. 18 and 19 show an embodiment similar to that of FIGS. 13-17 but wherein there is no enlarged opening in haptics 68, 70.

Referring to FIG. 17, a modified form of the ridges 38, 40 at the ends of the optic extensions are hollow with passages 76, 78 therethrough, as shown in FIG. 17. As indicated in the figure, this type of ridge portion enables the ridge portion to be compressed by application of pressure to facilitate installation and retention of the ridge in a slit 64 or 66.

FIGS. 20-26 illustrate embodiments in each of which relatively rigid frame members have attached therebetween a web whereon is disposed an optic.

FIGS. 20-22 show an embodiment 80 wherein web 82 is secured to opposite frame members 84, 85, as by integral molding of the components, by fasteners 86, or spot-welding. An optic 88 may typically be formed integrally with the web. The rigid frame members include transversely extending end loops 90, 92, as shown, for centration of the optic in the capsular bag of an eye.

FIGS. 23-26 illustrate an embodiment wherein spaced-apart relatively rigid frame arms 96, 98 have attached thereto end portions of arms of webs 100, 102 which extend oppositely from a haptic 104. The webs are typically formed integral with the optic. The webs have retention knobs 110, 112 on their end portions (FIG. 26) to engage in slots 106, 108 in the frame arms to secure and retain the web portions relative to the frame members.

FIGS. 24 and 25 are side views, taken respectively at lines 24 and 25 in FIG. 23, showing the particular manner in which the lugs 110, 112 engage in the slots 106, 108, and the relation of the optic to the frame members.

It will be understood that various changes and modifications may be made from the preferred embodiments discussed above without departing from the scope of the present invention, which is established by the following claims and equivalents thereof.

What is claimed is:

1. An intraocular lens assembly for increased depth of focus, comprising:
    a frame having haptics extending oppositely and longitudinally, said haptics having lateral edges disposed on an outer periphery of the frame, said frame being configured to vault posteriorly in an eye of a person,
    said frame having end portions to engage in the periphery of the capsular bag of an eye,
    said frame defining a generally circular opening disposed through said frame, said opening positioned between inner portions of said haptics,
    an optic sized and configured to engage in an edge portion of said frame opening, and
    interengaging features on the frame and on the optic for attachment of the optic to the frame for limited optic movement relative to the frame, said interengaging features comprising transverse slots in the frame spaced oppositely from said opening, and mounting portions extending oppositely from the optic and having transverse ridges at end portions thereof for retention in the slots, at least one of said slots has a widened portion with slot end shoulders to retain at least one of said ridges for prevention of optic lateral movement, and a portion of the haptic between each slot and said frame opening having a reduced longitudinal dimension to facilitate folding of the frame longitudinally for insertion of the frame through a slit in an eye,
    whereby light refracted by the cornea of the eye travels an increased distance to the optic to substantially increase depth of focus.

2. An intraocular lens assembly for increased depth of focus, comprising:
    a frame of generally rigid material and configured to vault posteriorly in an eye of a person, said frame having haptics extending oppositely and longitudinally, said haptics having lateral edges disposed on an outer periphery of the frame,
    said frame defining a central generally circular opening disposed through said frame,
    said frame having transverse slots spaced oppositely from said frame opening, and
    an optic adapted to be disposed adjacent said frame opening, said optic having mounting portions extending oppositely therefrom for engagement in said frame slots to retain the optic relative to the frame wherein an enlarged opening is defined in each of said haptics, and extends into proximity with said slots to define a substantially narrow hinge portion to facilitate bending of the lens along its longitudinal axis,
    whereby light refracted by the cornea of the eye travels an increased distance to the optic to substantially increase depth of focus.

* * * * *